United States Patent
Allotta et al.

[11] Patent Number: 5,916,146
[45] Date of Patent: Jun. 29, 1999

[54] SYSTEM FOR SUPPORT AND ACTUATION WITH VERTEBRAE IN PARTICULAR FOR SURGICAL AND DIAGNOSTIC INSTRUMENTS

[75] Inventors: Benedetto Allotta, Pisa, Italy; Luca Passaggio, Lugano, Switzerland

[73] Assignee: Bieffe Medital S.p.A., Grosotto, Italy

[21] Appl. No.: 08/894,514

[22] PCT Filed: Dec. 18, 1996

[86] PCT No.: PCT/IB96/01445

§ 371 Date: Aug. 21, 1997

§ 102(e) Date: Aug. 21, 1997

[87] PCT Pub. No.: WO97/23158

PCT Pub. Date: Jul. 3, 1997

[30] Foreign Application Priority Data

Dec. 22, 1995 [IT] Italy ................................. MI95A2724

[51] Int. Cl.[6] .................................................... A61B 1/00
[52] U.S. Cl. .......................................... 600/141; 600/139
[58] Field of Search ..................................... 600/139, 140, 600/141, 142, 143, 144; 138/118, 120, 155

[56] References Cited

U.S. PATENT DOCUMENTS

| | | |
|---|---|---|
| 5,042,707 | 8/1991 | Taheri . |
| 5,271,381 | 12/1993 | Ailinger et al. . |
| 5,759,151 | 6/1998 | Sturges ................................ 600/139 X |

FOREIGN PATENT DOCUMENTS

| | | |
|---|---|---|
| 0095970 | 12/1983 | European Pat. Off. . |
| 448284 | 3/1991 | European Pat. Off. ............... 600/141 |
| 0626604 | 11/1994 | European Pat. Off. . |
| 2143920 | 2/1985 | United Kingdom ................... 600/141 |

*Primary Examiner*—Beverly M. Flanagan
*Attorney, Agent, or Firm*—Ostrolenk, Faber, Gerb & Soffen, LLP

[57] ABSTRACT

A system to actuate and support surgical diagnostic flexible and orientable instruments of the endoluminal and/or endoscopic type, comprising at least a distal part, a proximal part and a medial part, characterized in that at least the distal part consists of vertebrae-like elements formed of portions of two dihedrals, delimited by a cylindrical surface, one of the dihedrals being convex with a projecting edge and belonging to a preceding vertebra, the other dihedral being concave, namely with a reentering edge, belonging to the successive vertebra.

16 Claims, 11 Drawing Sheets

SYSTEM FOR SUPPORT AND ACTUATION WITH VERTEBRAE IN PARTICULAR FOR SURGICAL AND DIAGNOSTIC INSTRUMENTS

BACKGROUND OF THE INVENTION

1. Field of the Invention

The present invention concerns systems, denoted in the following with the acronym SAV, for supporting and actuating, in particular, surgical and diagnostic instruments, limb prostheses, toys, diagnostic instruments for the industrial field, etc. The systems include mechanical elements, i.e., links, generally equally arranged in vertebrae fashion, and a group of cables.

In a preferred general embodiment of the invention, the vertebrae links are arranged serially so as to form a three-dimensional open kinematic chain, wherein every vertebra (1b) forms, along with the preceding vertebra (1a), a rotational kinematic pair with an excursion, generally symmetric, having an angle in the range of $\pm\alpha$ and constituting an elementary module in which the following (SUCC) vertebra (1b) has two directions of rotation with respect to two mutually orthogonal axes, both orthogonal to the axis of the preceding (prec) vertebra (1a), named P and Y (Pitch and Yaw). The actuation of these two movements is performed by means of cables (7) associated with the kinematic chain of vertebrae.

2. Description of the Related Art:

The need for systems for support and actuation with a high level of articulation becomes more and more intense as technology evolves along with the related increase in sophisticated user demands. To cite some examples, in many surgical interventions it is necessary to introduce instruments inside the human body with the aim of observing the operating scene by means of suitable optics and/or of intervening with tools. The instruments devoted to this goal are formed by a distal end, a medial shaft and a proximal end. The instruments are grasped by an operator in the neighborhood of the proximal end whereas the optics and the tool are in the distal end. Although in some procedures it is sufficient to use instruments having a rigid medial shaft, in most cases it is necessary that the instruments possess a certain amount of dexterity in the distal end, which typically results in an increase in the invasivity of the procedure or, even worse, the impossibility to execute it. In flexible steerable endoscopes, (colonoscopes and gastroscopes) it is possible to steer the tip of the distal end of the instrument.

A flexible steerable endoscopic instrument has a circular section and includes a proximal end, a distal end and a flexible shaft connecting the proximal end and the distal end. The curvature of the distal end can be modified by means of a suitable actuation system, normally including a set of sheathed wires, controlled by the operators by means of wheels located in the handle. The proximal end of the instrument is attached to the handle. In this way it is possible to steer the tip of the distal end in a desired arbitrary direction. The flexible shaft, in addition to housing the sheathed actuation wires, possesses some channels located close to the longitudinal average curve of the instrument. Such channels can be used for passing-through fiber optic and/or mechanical transmission means devoted to the actuation of an instrument attached to the distal end.

Flexible steerable endoscopes are used for diagnostic purposes and for this reason an optical channel (usually an optic fiber) allows both the illumination of the body part to be explored and the transmission of images thereof. They can also be used as surgical instruments in the case where they have an operating channel which allows the introduction of a suitable tool (gripper, scissors, electro-scalpel, electro-coagulator, etc.).

In European Patent No. 0 427 949, the Applicant has already described a circular stapler featuring a suturing head located in a suitable location, for example, mounted at the end of a flexible shaft consisting of at least a traction wire and spherical joints, preferably made of polymeric material.

An example of an endoluminal steerable circular stapler is shown in European patent application EP 0 540 020 A2 (FIGS. 1 and 1A). The inventors, however, do not specify either the kinematic configuration or the constructive solution used to implement the distal steerable end.

In U.S. Pat. No. 5,383,880 a linear staple with a flexible shaft actuated by means of an electric motor placed in the handle is described. Sensors are present to allow control through a dedicated unit. The system, however, lacks the possibility to purposely steer the end tool placed in the distal end of the instruments. Furthermore, it is not possible to change the end tool easily, during an intervention, in order to execute several sutures. The description of the sensory given in the "Detailed Description of the Invention", is generic and does not clearly explain which parameters are used and how to measure them.

An example of actuation with vertebrae is shown in International Patent Application No. WO 92/01414 (FIG. 2A) where the vertebrae forming the structure of the distal end are articulated by means of spherical joints allowing also a rotation of a vertebra with respect to the axis of the preceding vertebra. Such rotation cannot be controlled by the actuation wires of the device and, as a consequence, it is impossible to obtain a suitable torsional stiffness. In the present invention, the kinematics of the articulations and the shape of each vertebra allows for obtaining suitable increased torsional stiffness.

Another example of a mechanism providing a solution to the problem of torsional compliance of the shaft of a steerable instrument is described in International Patent Application No. WO 94/17965 (FIG. 1): the mechanism is planar and consists in a chain of articulated, crossed four bar linkages with rigid links allowing to change the curvature of the linkage in its plane under the power of a suitable actuator. This solution ensures adequate stiffness in any direction, but it is planar, so it allows only steering of the instrument tip in a plane.

The system described in International Application No. WO 90/05491 (FIG. 1) includes a steerable distal end made with vertebrae that allows for placement of a tool for the application of a staple for aneurysm. The vertebrae configuration does not allow correct kinematic operation of the mechanism because the average curve changes its length during operation. As a consequence of the change in the length of the average curve of the instrument, the instrument itself is not suitable for guiding fiber optics. In addition, another consequence of the change in the length of the average curve is that the actuation cable passing through the vertebrae is deformed as a consequence of bending of the instrument, and this may cause improper and/or undesired operation of the actuated tool.

SUMMARY OF THE INVENTION

The present invention provides actuation and support systems that do not have the disadvantages of conventional systems, in particular those of the known instruments mentioned above, with respect to which it has some advantageous and differentiating features previously outlined. The most important of these features can be derived from the patent claims.

Figure 6:
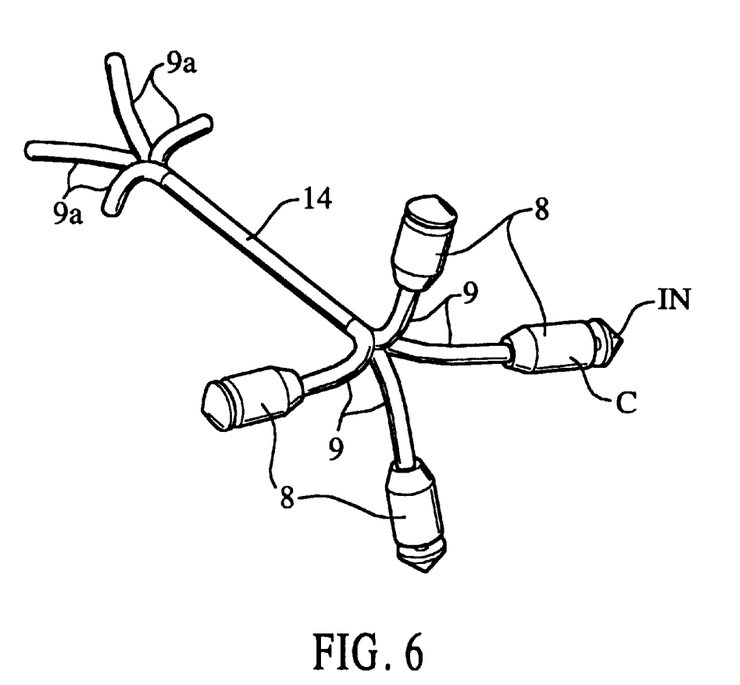
FIGS. 6 and 7 are two perspective views of SAV systems according to the invention associated with an endoluminal circular stapler and to the distal part of a tool-holding instrument.
Figure 7:
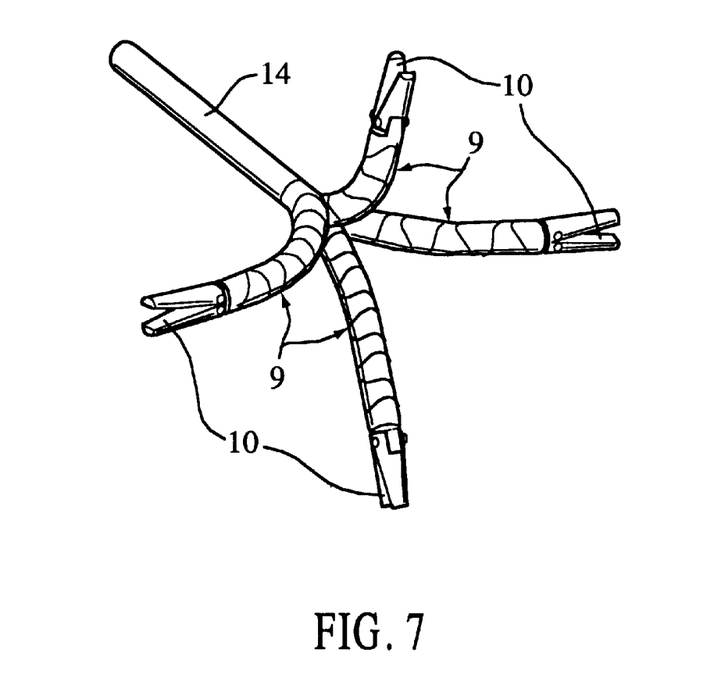
Figure 9:
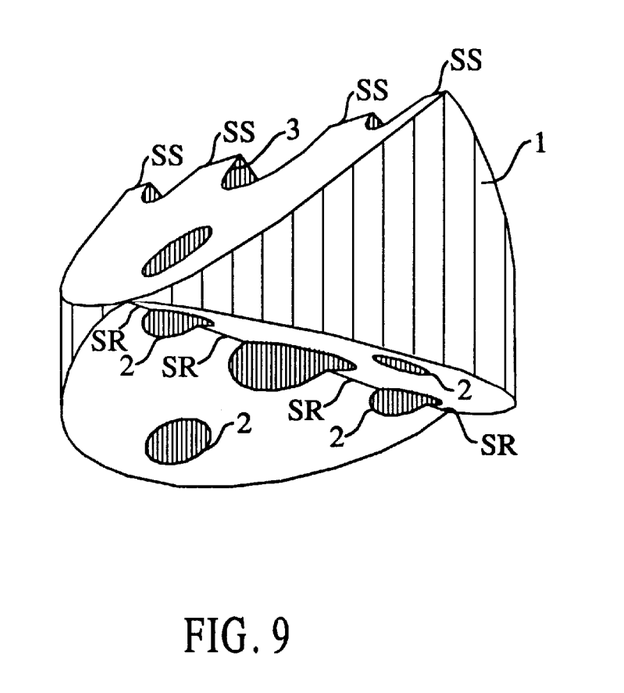

In the present invention, the chosen kinematics and the chosen constructive solution allow for steering the tip of the instrument in any direction and not only in a plane. Indeed the SAV, according to the invention, can bend in any plane passing through the longitudinal axis of the underformed mechanism as shown in FIGS. 6, 7 and 9, and it can consequently steer the optics and the tool in a desired fashion along two arbitrary desired angles of pitch and yaw (P and Y). In addition, the structure of the SAV, according to the invention, ensures a sufficient stiffness in any direction.

In the SAV according to the present invention, the average curve of the instruments maintains its length constant during bending, allowing the use of fiber optic and/or actuation wires and/or pneumatic tubes and/or hydraulic tubes in the neighborhood of the average curve.

BRIEF DESCRIPTION OF THE DRAWINGS

The aspects and advantages of the invention will appear in a clearer manner from the implementations represented (illustratively and not limitatively) in the accompanying drawings.

DETAILED DESCRIPTION OF THE PREFERRED EMBODIMENTS

The system for Support and Actuation with Vertebrae according to the invention is formed by a set of n pairs of mechanical elements (links), normally equal, named vertebrae (1) and a set of, for example, 4 cables (7). The vertebrae (1) can be assembled so as to form a SAV (9) (see FIGS. 6, 7, 9) of desired length. The SAV can be in particular used to form the distal part (5) of a surgical or diagnostic instrument (FIGS. 5, 6, 7) with flexible shaft (7) and steerable end (5), or a surgical or diagnostic instrument with rigid shaft and steerable end.

Figure 4:
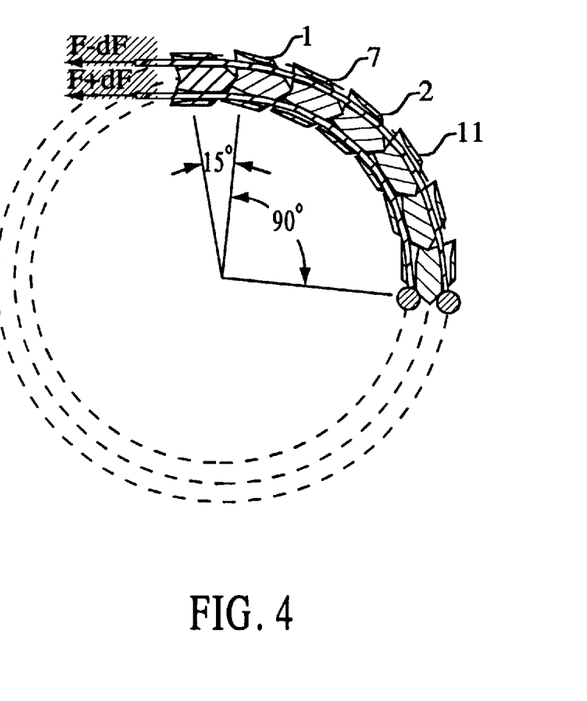
FIG. 4 shows a partial cross-sectional view of a SAV system according to the invention, formed by pairs of vertebrae, as shown in FIGS. 2 and 3, and by cables.

The vertebrae (1), arranged in serial fashion, form a three-dimensional kinematic open chain (11) as shown in FIG. 4. Every vertebrae (1b) forms, together with the preceding one (prec), a rotational joint with a symmetric stroke equal to $\pm\alpha$, where $\alpha$ is the angle defined in the following. A set of two vertebrae (1a) and (1b) is an elementary module that allows two rotations of the following vertebra (1b) with respect to two mutually orthogonal axes named Pitch and Yaw (P and W).

Figure 2:
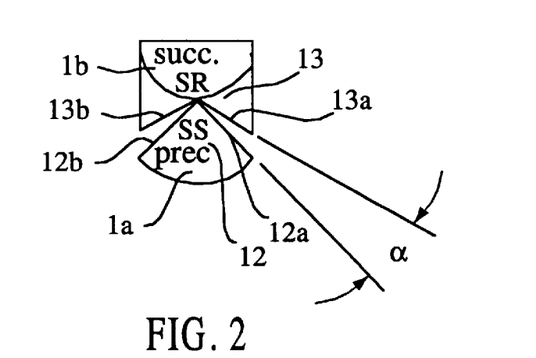
FIG. 2 shows a partial schematic lateral view of a pair of vertebrae.

The kinematic structure formed by 2n rotational joints with rigid links is widely used in endoscopy. Conventionally the rotational joints are normally constructed with shafts and miniaturized bearings and, hence, expensive to manufacture and assemble. The system for Support and Actuation with Vertebrae (SAV) according to the invention is advantageous with respect to existing endoscopic systems because the implementation of rotational joints is done, in the base version, by means of a convex solid dihedral (12), i.e., with a protruding edge (SS) given by the intersection of the two sides of the dihedral angle (12a) and (12b), being the width of the convex dihedral angle (12) equal to $2\beta$ and machined in the preceding vertebra (1a). The convex solid dihedral (12) machined in the preceding vertebra (1a) can be coupled with a concave solid dihedral of width equal to $2(\beta+\alpha)$ machined in the following vertebra (1b), as shown in FIG. 2, which represents a rotational joint formed by the dihedral, namely the convex one (12) and the concave one (13), belonging to the two adjacent vertebrae (1a) and (1b).

If the two vertebrae (1a) and (1b) are undeformable, the relative motion of a vertebra (1b) with respect to the preceding one (1a) is a rotation $\Theta$ in the range $[-\alpha; +\alpha]$ with respect to the common edge SS=SR of the convex solid dihedral (12) and concave solid dihedral (13). The system features performances similar to those used until now in endoscopy, either in terms of mobility or in terms of precision, with the advantage of a big simplification both in the construction (all the vertebrae are alike) and in the assembly phase.

Robustness, simplicity and low cost of the SAV system according to the invention allow its use not only in traditional endoscopic instruments but also in disposable instruments.

The SAV system according to the invention can be used as a hand-controller interface to be mounted on the handle (6) of an instrument with a steerable end (5). If the two SAVs, i.e., the distal one (9), devoted to steer the end tool, or the optics, and the proximal one (9a), are connected by sheathed cables (7), they are deflected in a countersymmetric fashion due to the undeformability of the transmission cables (7), according to the scheme shown in FIG. 5. In addition, if the sheathed transmission cables are twisted along the medial part (14) of the instrument, it is possible to obtain also a symmetric deformed configuration.

An application example of the SAV is given in FIG. 6 where the distal end of a steerable endoluminal circular stapler is shown. It is possible to steer the suturing tool (8) containing the staples by means of a SAV.

Another application example of the SAV is given in FIG. 7 where the distal end of a multipurpose instrument with a laparoscopy micro gripper (10) is shown. The micro gripper can be steered by means of a SAV (9). Similarly to what is shown in FIG. 7, it is possible to use the SAV to construct multipurpose instruments where one could change the end-tool (electrical scalpel, scissors, grippers, etc.).

A possible use of the SAV system is the construction of artificial hand fingers for prosthetic applications. Using two or more SAV systems, it is possible to construct polyarticulated gripping devices.

Figure 1:
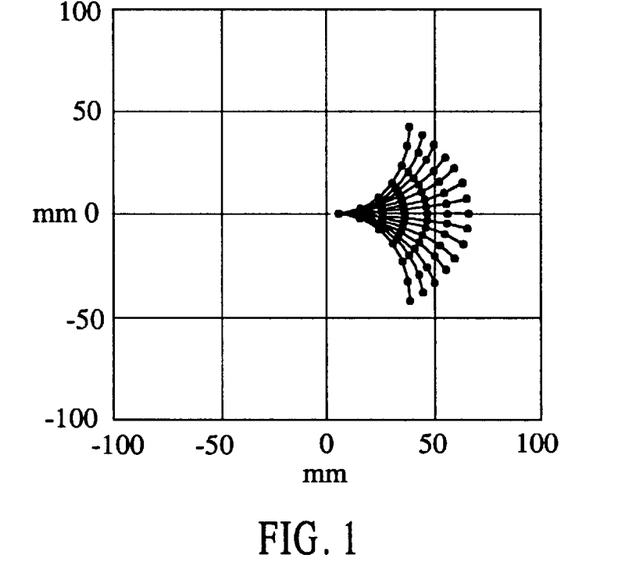
FIG. 1 is a schematic lateral view of a SAV system shown in a Cartesian diagram where axis X and axis Y correspond to depth "p" (measured along the penetration direction) and deflection "def" of the tip of the SAV, measured as displacements from the rectilinear configuration "def"

A further use of the SAV is the construction of toys for children. A possible configuration can be devised with two SAVs: the first SAV (distal SAV) is used to steer a doll, while the other one (proximal SAV) is used as a hand-controller interface, according to the scheme shown in FIG. 5. To summarize, FIGS. 1–9 give the following representations:

FIG. 1 shows some of the possible planar configurations of a group of six elementary (i.e., 12 vertebrae elements (1)). In the shown case, only as an example, every joint allows a maximum rotation ±α with α=15°.

FIG. 2 shows a rotational joint formed by a convex solid dihedral angle (12) belonging to the preceding vertebrae (1a) in contact with a concave solid dihedral angle (13) belonging to the following vertebrae (1b) along the common edge (SS=SR) of the two dihedral angles.

Figure 3:
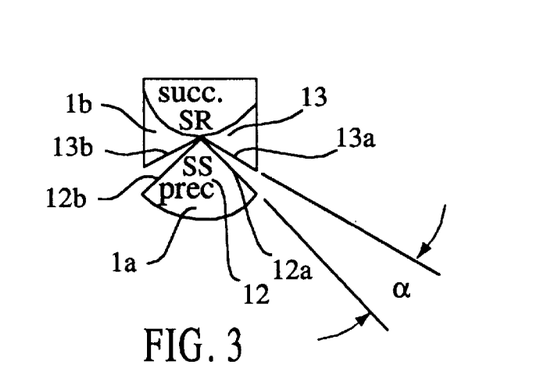
FIG. 3 shows a partial schematic lateral view of a pair of vertebrae shown in FIG. 2.

FIG. 3 shows a modified version for heavy loads of FIG. 2.

FIG. 4 represents a cross-sectional view of a SAV along one of the infinite planes of possible bending. The bending of the SAV along one of the infinite planes of possible bending is obtained, in the shown example, by means of two pairs of pre-tensioned cables (7) passing through holes of suitable shape (2) machined in every vertebra (1), similar to the elements of a chain.

Figure 5:
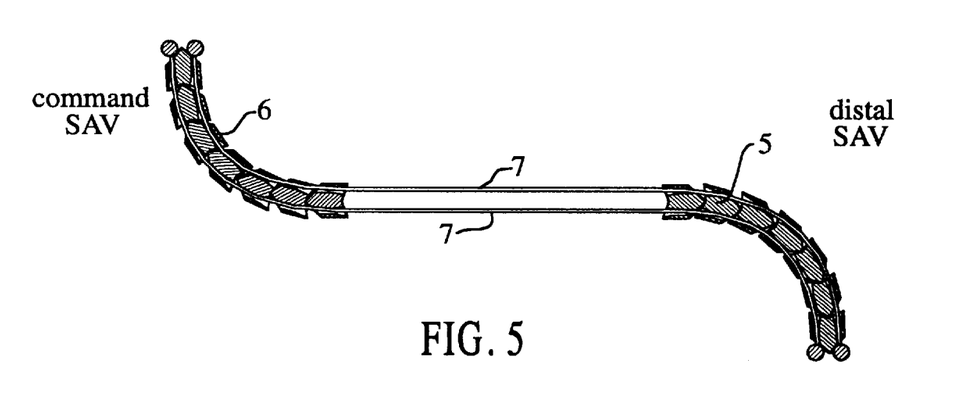
FIG. 5 shows a schematic cross-sectional view (similar to the one in FIG. 4) of two SAV systems according to the invention, namely a distal SAV and a proximal SAV, connected by means of sheathed cables where the distal SAV acts like an operative end of the instrument and the proximal SAV acts like a hand controller.

FIG. 5 shows in particular that the SAV according to the invention can be used like a hand-controller interface to be mounted on the handle of an instrument with steerable distal part (9), consisting itself in a SAV. Indeed, if the two SAVs, namely, the distal one (9) devoted to steer the end tool and/or the optics (not shown here), and the proximal one (9a) devoted to the control of the steering, are connected by means of sheathed cables (7) belonging to the medial part of the instrument (14), they shall deflect in a symmetric fashion due to the undeformability of the transmission cables (7), according to the scheme shown in FIG. 4.

FIG. 6 shows an example of application of a SAV according to the invention to the design of an endoluminal circular stapler with a steerable end tool. A suturing tool (8) including a cartridge containing the staples (C) and an anvil (IN) is mounted on the tip of the distal SAV (9). In the drawing, as an example, four of the infinite possible deformed configurations that the distal part of the instrument may assume are shown.

FIG. 7 shows an example of use of the SAV for the design of the distal part of a multipurpose instrument where it is possible to mount various tools. In the drawing is shown, as an example, the distal part of such an instrument, including a SAV (9) holding a laparoscopy gripper (10).

Figure 8:
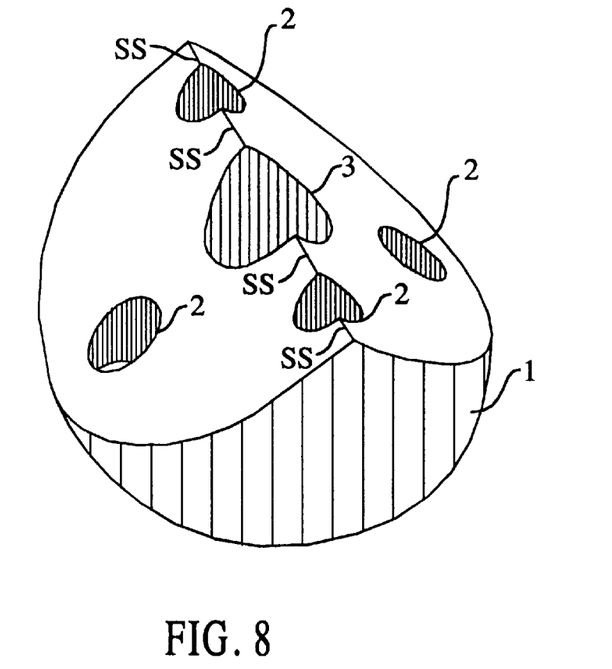
FIGS. 8 and 9 are two perspective views from two different viewpoints of a vertebra according to the invention.

FIG. 8 shows a prospective view of a vertebra (1): it is possible to distinguish holes (2) for the transmission cables (7) of the SAV and a central hole (3) devoted to fiber optic and/or hydraulic tubes and/or pneumatic tubes devoted to the actuation of the end tool mounted on the tip of the SAV. It is also possible to distinguish the protruding edge (SS) of the convex solid dihedral angle (12) devoted to be inserted in the concave solid dihedral angle (13) belonging to the following vertebra (1b).

FIG. 9 shows a perspective view of a vertebra (1): it is possible to distinguish holes (2) for the transmission cables (7) of the SAV and a central hole (3) devoted to fiber optics and/or hydraulic tubes and/or pneumatic tubes devoted to the actuation of the end tool mounted on the tip of the SAV. It is also possible to distinguish the protruding edge (SS) of the convex solid dihedral angle (12) devoted to be inserted in the concave solid dihedral angle (13) belonging to the following vertebra (1b). It is also possible to see the edge (SR) belonging to the concave solid dihedral angle (13).

The SAV are best used in steerable flexible surgical instruments (indicated as "steerstap") consisting of a handle, a control interface, a flexible arm and an orientable end in which it is possible to dispose: a circular steerstap, i.e., a tool to make sutures within a lumen by means of metallic staplers arranged according to a circular pattern; or a linear steerstap in which the staplers are arranged according to a linear pattern. Steerstap are presently sought in which the operating tool is orientable in addition to the orientation of the flexible arm to facilitate the tool insertion inside the lumen when a circular cartridge is used, or to realize the suture with the best orientation in case of a linear cartridge.

Figure 10A:
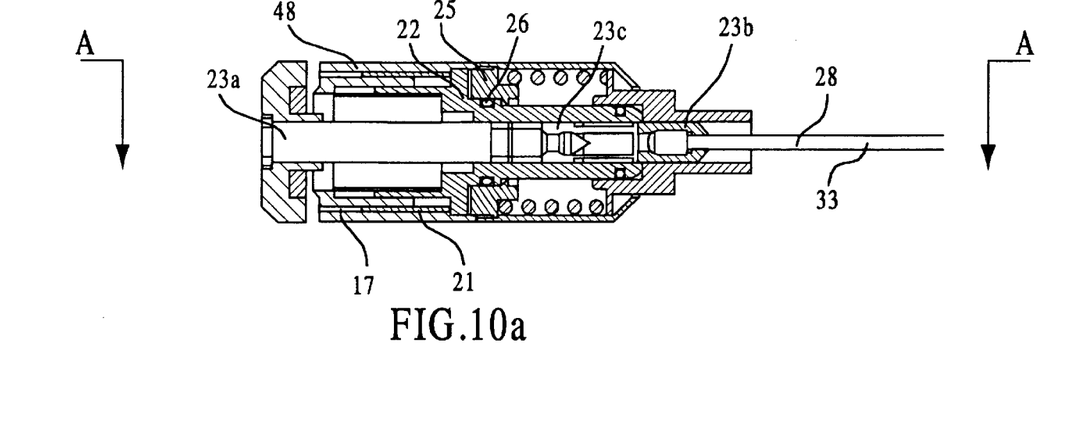
FIGS. 10a and 10b are cross-sectional views (according to lines A—A and B—B) of a circular cartridge (8 in FIG. 6)
Figure 10B:
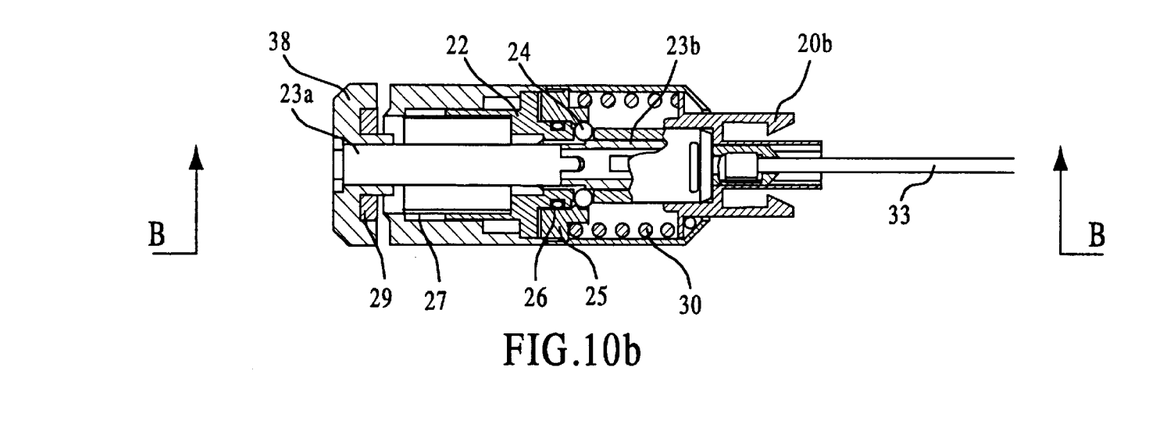

FIGS. 10 and 10A show a preferred embodiment of a circular cartridge, consisting of an anvil 38 and staple holder 48 within which are contained the metallic staples. To the mandrel (23) can be connected the anvil 38 which is pushed against the staple holder by the two anvil forming elements 23a and 23b which are assembly disconnected. The staples 17 are pushed against the anvil 38 through the stapler pusher (21) activated, on its turn, by the hammer 22 which can be mounted on the steerstap distal end 9 by means of a rapid engagement system (20b) and can be decoupled by means of a dedicated key 31.

The mandrel (23a, 23b) is activated by a driving covered cable (28) within the flexible arm of the device (14) and of the steerable distal end (9). To allow a correct approach of the tissue pieces (32) to be sutured before the application of the staples 17, the hammer 22 shows two safety systems which inhibit the stapler holder (8b) before which a right compression of the tissue (32) is obtained with or without the surgeon choice. The first safety system consists of the spherical balls (24) which in the non-optimal conditions of the staple application engage the staple-holder (8b). Such a safety system is set off by means of cams (23c) which are integral with the mandrel (23a) and allow that, once the distance between anvil (8a) and staple holder (8b) is appropriate, the balls (24) go near the circular cartridge central axis and make free the sliding of the hammer (22) over the staple holder (8b) and the consequent application of staple (17).

The second safety system consists in a calibrated force that the surgeon has to overcome to activate the cartridge after which the correct suture distance (d des) has been reached and the first safety system of the circular cartridge has been deactivated. At this point, the surgeon can carry out the suture after which he has overcome the threshold of the above-mentioned set force exerted by the spring (26) preferably of the type "Bal-Seal".

Figure 11:
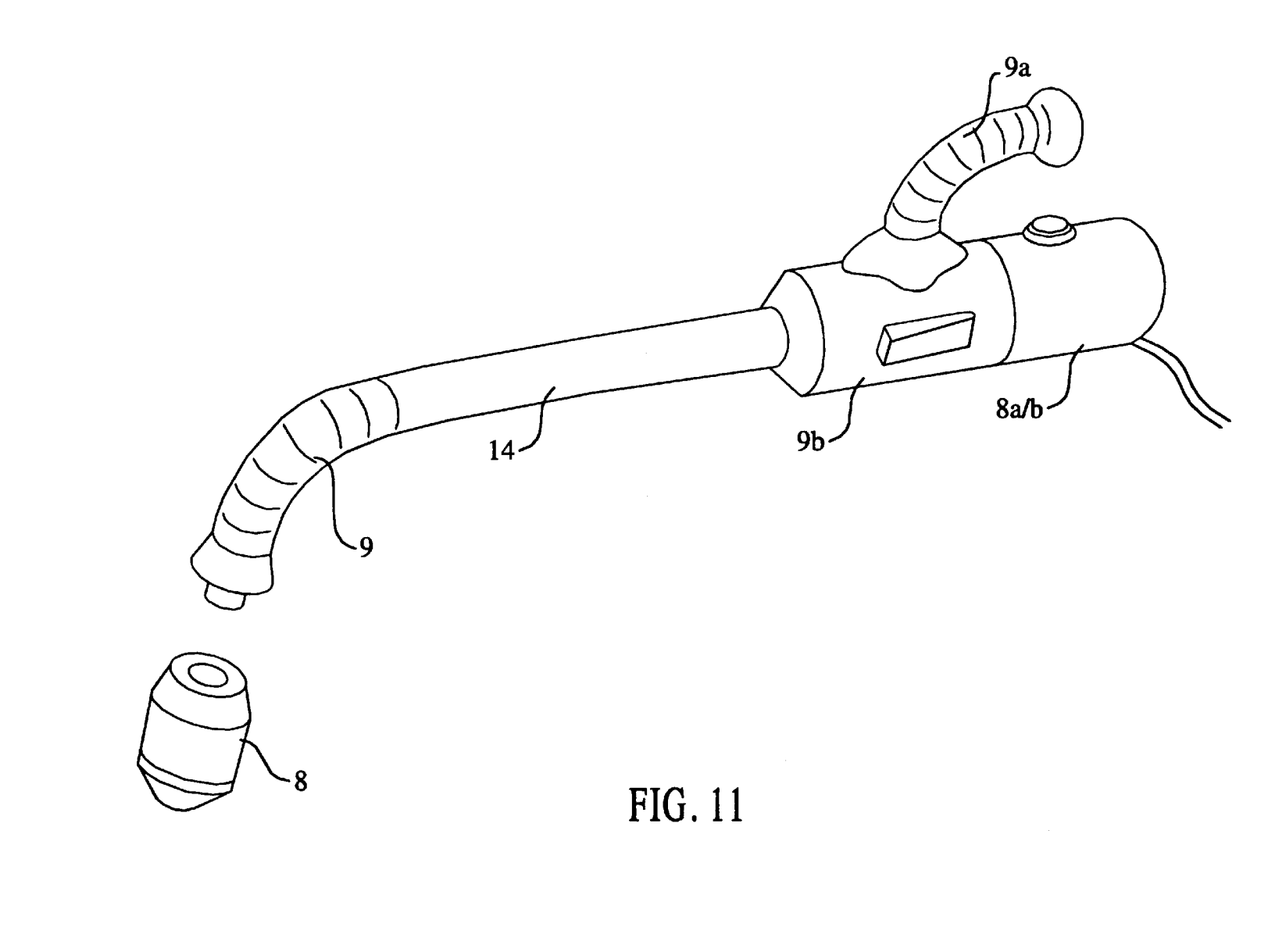
FIG. 11 is a perspective view of an embodiment of a system according to the invention comprising the proximal vertebra mechanism 9a, the flexible medial part 14, the actuated distal vertebra mechanism 9, with the addition of a brake 9b, the command mechanism 8a acting on the distal (circular) cartridge 8, the mechanism 8a being manual or motorized, as shown in FIGS. 12 and 12a which are schematic cross-sectional views of a manual, respectively motorized, handle.

FIG. 11 shows a system to activate a cartridge (8, e.g., circular) comprising the proximate vertebra mechanism (9a), the flexible medial part (14), the vertebrae actuated distal mechanism (9).

Figure 12:
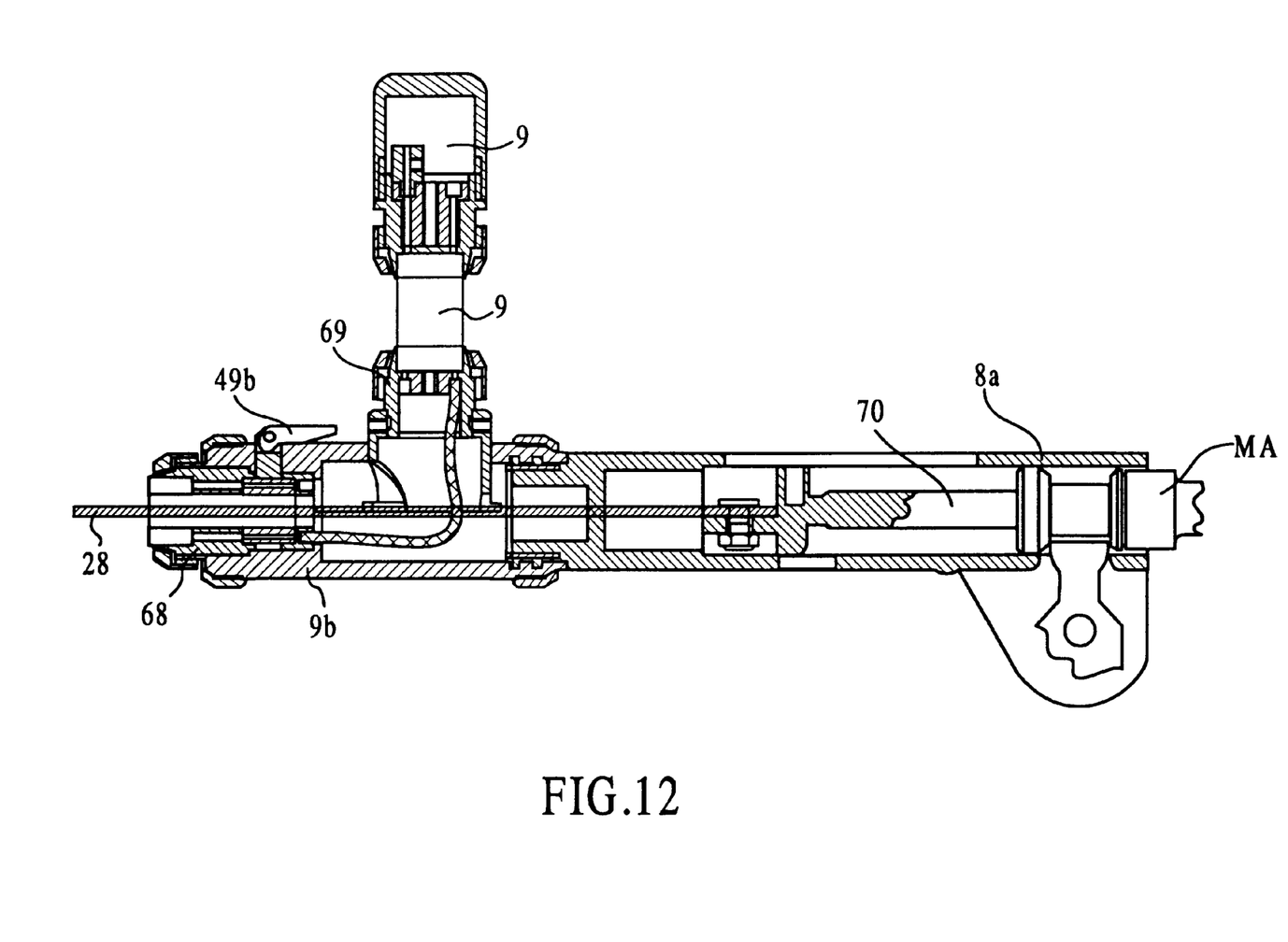

Typically a brake (9b) is added in the proximal part (9a), to maintain the geometrical configuration of the actuated distal part (9), established by the operator in approaching the tissue to be stapled; characteristically at the rear end of the brake (9b) is placed a device (8a) to actuate the cartridge (8) mechanism, the device being manual or motor activated. The manual device is shown in the cross-section vie of FIG. 12 comprising substantially the brake lever 49 (b) generating a transverse load on the command wires or cable (7), the frontal flange 68 connecting the medial part (14) to the complex brake body (9b). The rotating flange (69) has the function to adjust the stroke of the proximal vertebrae mechanism (9a) to the stroke of the distal vertebrae mechanism (9). On the rear part of the brake body (9b) is shown a typical implementation of the cartridge actuator device (8a) manually activated. This device can be conventional, for example, such as of the type described in European Patent No. 0 427 949.

Figure 12A:
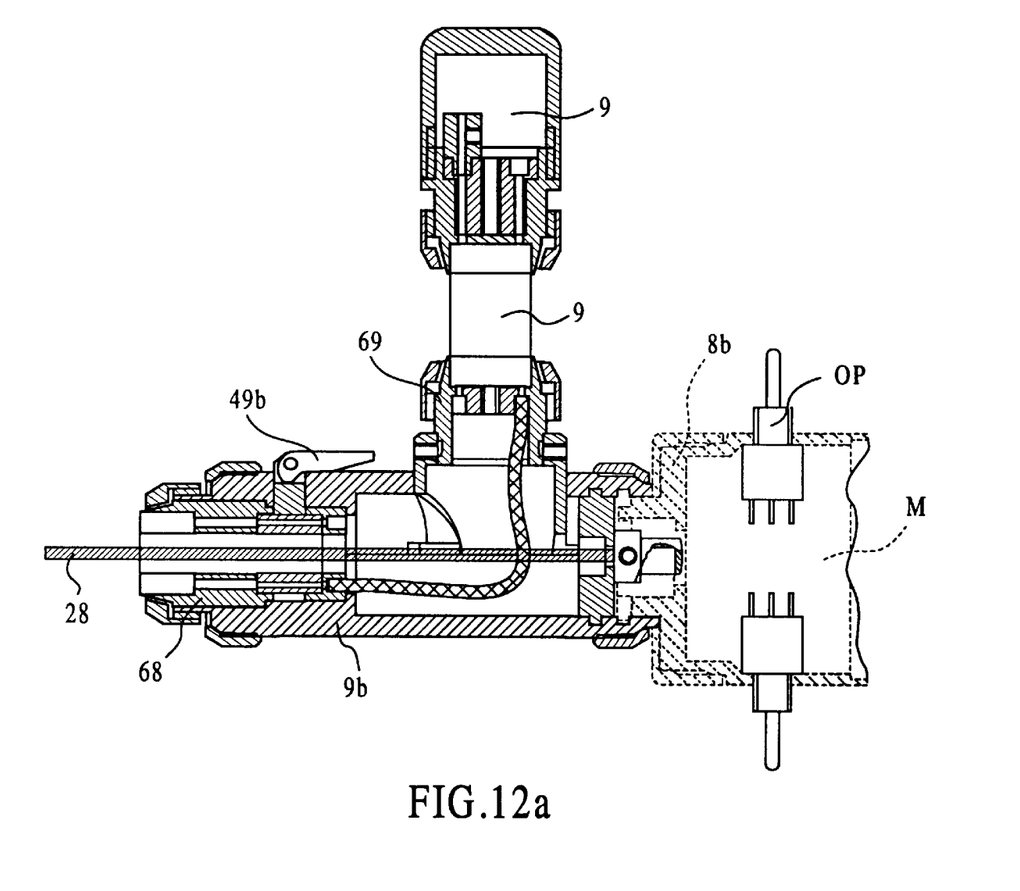

FIG. 12A is the device (8b) in the motorized version (8b); the motor M is either within the cavity 95 having the operator switches OP on its outer surface, or at a remote position. The motorized device (8b) can be easily coupled or disconnected from the brake body (9b). Generally the motor holding device (8b) is sterilized after each operation to be immediately reused while the whole remaining is disposable.

Figure 13:
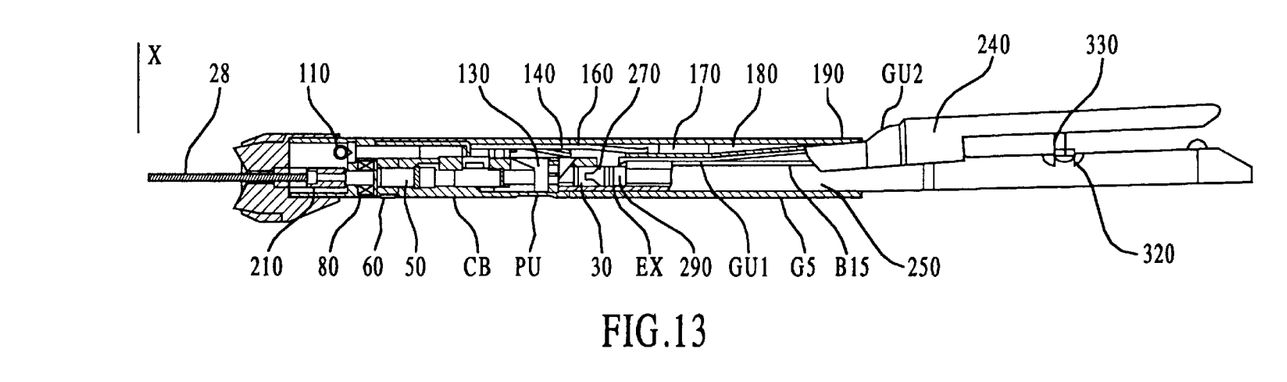
FIGS. 13 and 14 are schematic cross-sectional views of a linear cartridge 8.
Figure 14:
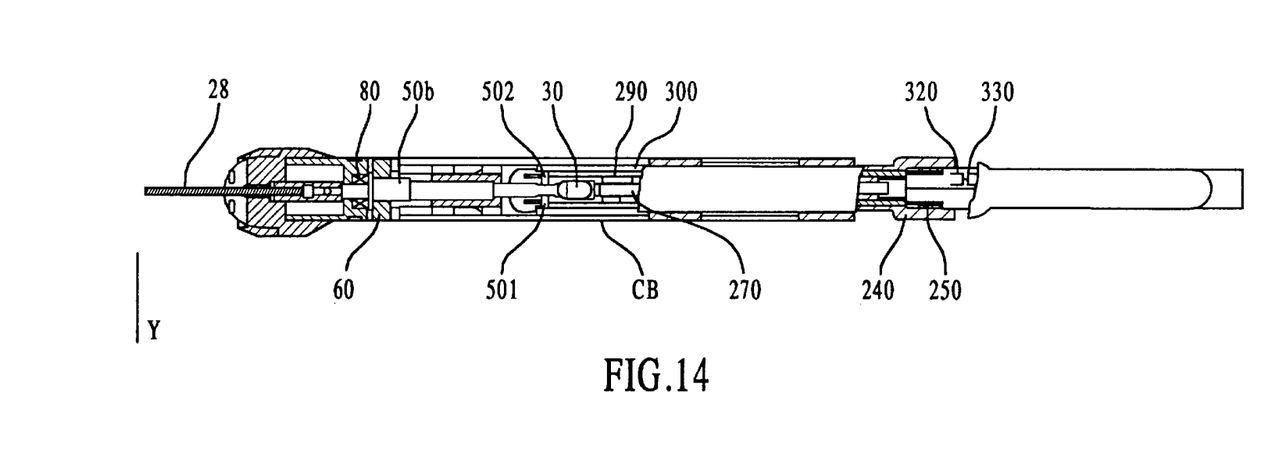

The linear cartridge shown in FIGS. 13 and 14 consists of at least a cartridge body (CB) supporting, in its distal end, two jaws (240) and (250) devoted to press the tissue to be stapled, and of mechanisms devoted to allowing the relative motion of the two jaws and to the execution of the suture.

Of the two jaws (240) and (250), one (250) denoted in the following as staple-holder, is devoted to hold metallic staples (330) for executing the suture, and mechanisms (BIS) to cut the tissue after suturing. The ejection mechanism (EX) consists of a threaded sleeve (290) which can slide but not rotate with respect to the cartridge body (CB). The threaded sleeve (290) is actuated by means of a screw (270) rotating with respect to the cartridge body (CB). A cutting device (BIS) and a pair of pushers (300) are fixed to the threaded sleeve (290). The pushers (300) cause the motion of suitable staple-ejectors (320) by means of cams. The staples (330) ejected by the staple holder (250) penetrate into the tissue and are deformed against the surface of the opposite jaw (240) in order to execute the suture according to the known technique. The staple holder (250) is linked to the cartridge body (CB) by means of a supporting guide (GS) whose internal surface has the same shape of the staple holder (250) external surface and by blocking mechanism (130) which can be released by the user by pushing a button (PU) thus allowing removal and substitution of the staple holder (250) when, after the execution of a suture, the user wants to execute a new suture. The other jaw (240), denoted in the following as anvil, is linked to the cartridge body (CB) by means of support (S01) and (S02), and guiding surfaces (GU1) and (GU2), so that the displacement of the guide (190) with respect to the cartridge body (CB) on the surface (GU2) results in a pivoting motion of the anvil (240) with respect to the guiding surface (GU1). The pivoting motion results in a closure motion of the jaws with compression of the tissue to be stapled and compression of a spring (MO) devoted to allow the opening motion of the jaws upon completion of the suture. The displacement of the guide (190) is actuated by means of a rotating screws (50) coupled with a second threaded sleeve (60) which cannot rotate with respect to the cartridge body (CB). The rotating screw (50) causes an axial motion of the sleeve (60) with respect to the cartridge body (CB), thus pushing ahead the tubes (160), (170), (180), and (190). Upon completion of the stroke necessary to close the jaws (240) and (250), the threaded sleeve (60) disengages itself from the screw (50) and loads the elastic element (40) which allows subsequent reengagement of the threaded sleeve (60) on the screw (50) when an inversion in the rotation direction of the screw (50) occurs. The backward motion of the threaded sleeve (60), due to the action of the spring (MO), causes the opening motion of the jaws (240) and (250) and the release of the tissue. Once the threaded sleeve (60) is disengaged from the screw (50), said screw (50) transmits its motion only to the small diameter screw (270) whose function has been described previously. Screw (50), supported by a ball bearing (80), or analogue device, is driven through the proximal clutch (210) and drives the rotation of the small diameter screw (270), supported by the staples holder (250), through the distal clutch (30).

The proximal clutch (210) transmits the torque from the screw (50) in both clockwise and counterclockwise directions by means of suitable coupling surfaces and/or by means of friction. Furthermore, the proximal clutch allows for compensation of uncertainties in the relative positioning of the two parts of the clutch. The distal clutch (30) transmits the torque from the screw (50) to the small diameter screw (270) in at least one of the two possible rotation directions, resulting in a rapid mounting device between the small diameter screw (270) and the screw (50). The screw (50) is driven by a transmission cable (28) sheathed within the flexible shaft (14) of the instrument and the steerable distal end (9); as an alternative, the linear cartridge can be mounted on the distal end of a rigid shaft.

The linear cartridge can be mounted on the distal end (9) of the steerstap by means of a rapid fastener (20b) and can be removed by means of a suitable tool (31).

A motorized handle (8b) or a manually actuated handle (8a), devoted to actuate the distal tool, can be mounted on the brake (9b). The motorized handle (8b) is mounted on the brake (9b) by means of a fastener in order to resterilize and reuse the motor in more interventions. A mechanical interface (MA) or an electronic interface (OP) allow the operator to control the approximation of the anvil (240 or 38) and staples holder (250 or 48) of either the circular cartridge or the linear cartridge and to command the ejection of the staples (17 or 330) and the execution of the suture.

Figure 15A:
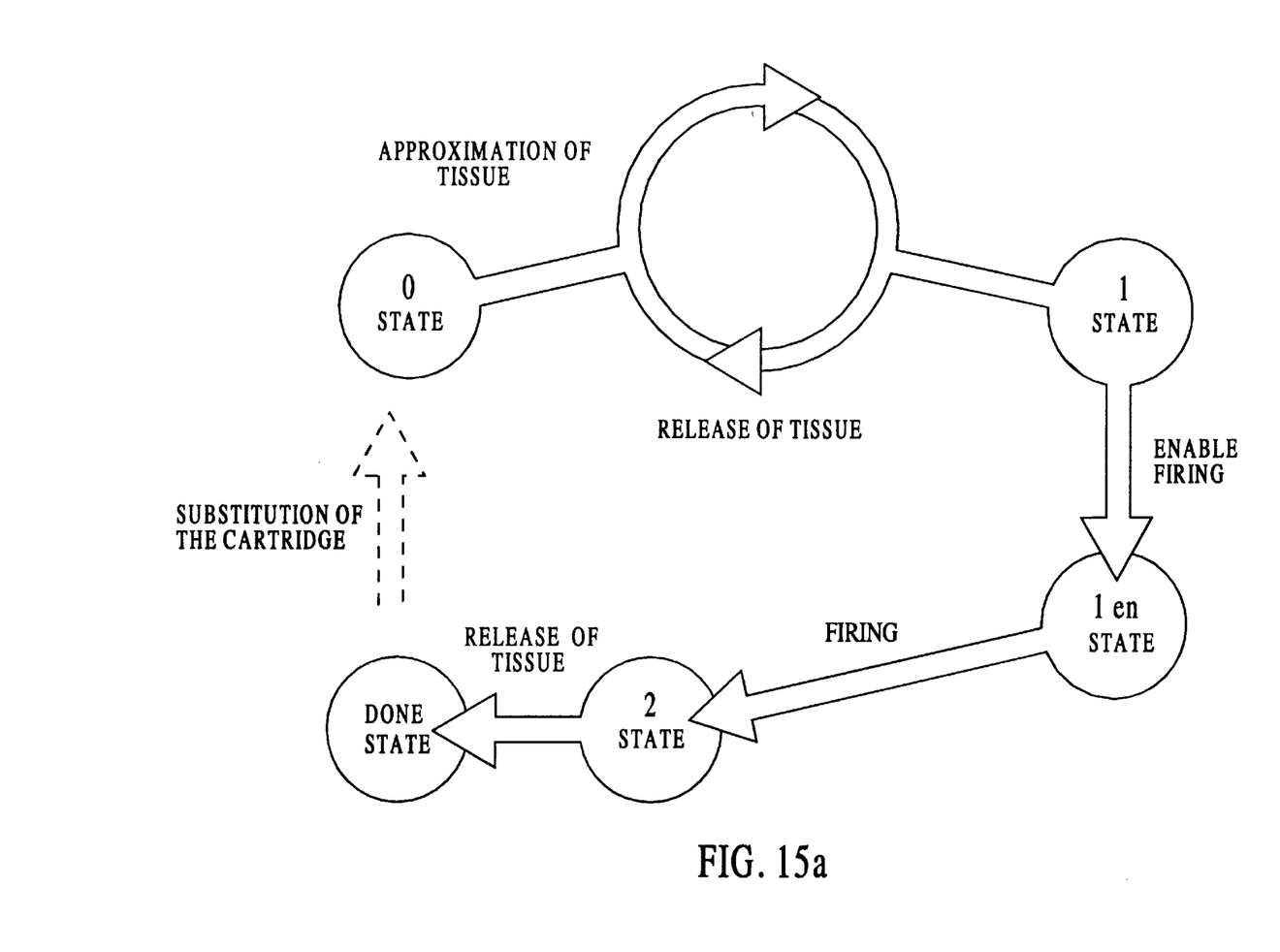
FIGS. 15a and 15b are graphical representations of task sequences to operate a suturing instrument equipped with the circular cartridge of FIGS. 10a and 10b or the linear cartridge of FIGS. 13 and 14.
Figure 15B:
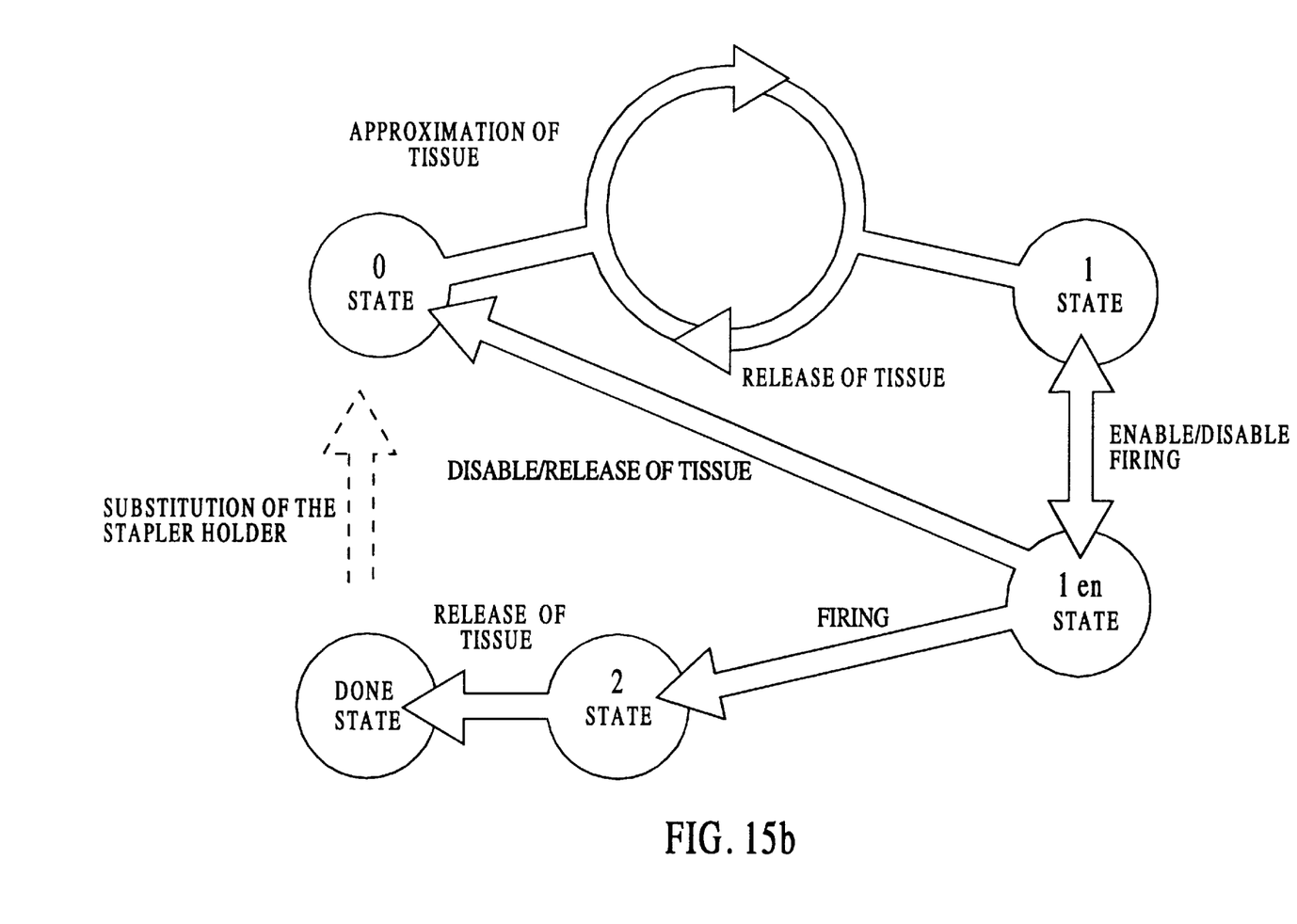

When the manually actuated handle is directly controlled by the operator, the motorized handle is controlled by means of a specific remotely or located device (CTRL), consisting in at least a microprocessor or other digital dedicated hardware, power supply, sensor interface, motor drive circuits and, optionally, in a display showing the process data and any other information valuable for the operator; the device (CTRL) accepting as input the operator commands given through the devoted interface (OP) and the motor position measured by a dedicated sensor placed on the motor shaft. In the case of a motorized handle, the device (CTRL) allows the operator to perform the predefined tasks sequences according to the control logic schematically depicted in FIG. 15 which is based on a position control of the transmission cable (28) and is implemented in suitable software, firmware or hardware.

FIGS. 15a and 15b show graphical representations of the tasks sequences required when operating suturing instruments equipped with the circular cartridge in FIG. 10a and FIG. 10b or the linear cartridge described in FIGS. 13 and 14. The operation on the stapler can be summarized by means of the five main logic states (state 0) (state 1) (state 1-en) (state 2) (state done) depicted in FIGS. 15a and 15b along with the possible paths between the main logic states: the stapler is in (state 0) when the anvil (38) or (240) is at the maximum distance from the staples holder (48) or (250) as during the approach to the tissue to be operated or at the end of the suture, when the tissue is released. The stapler is in (state 1) when the anvil (38) or (240) and the staples holder (48) or (250) are at the correct position to operate the suture, that is, the tissue to be operated is correctly compressed and the staples (17) or (330) can be ejected.

The manually operated stapler is in (state 1-en) when (state 1) has been reached and the operator overcomes a predefined force threshold calibrated through the mechanism (26).

The motorized staple is in (state 1-en) when (state 1) has been reached and the operator enables firing of the staples by means of the electronic interface (OP).

Although the present invention has been described in relation to particular embodiments thereof, many other variations and modifications and other uses will become apparent to those skilled in the art. Therefore, the present invention is to be limited not by the specific disclosure herein, but only by the appended claims.

We claim:

1. System for support and actuation of endoluminal and/or endoscopic surgical and diagnostic instruments, the system comprising:

a distal part;

a proximal part; and a medial part connectively disposed between the distal and proximal parts, the distal part including a plurality of vertebral elements, each vertebral element being formed by vertebra portions having opposed ends formed in the shape of two solid dihedral angles, wherein:

one of the two ends has a dihedral angle which is convex, has a protruding edge, a width $2\beta$, and is connected flexibly with a proximally adjacent one of the plurality of vertebral elements; and the other end has a dihedral angle which is concave, a width equal to $2(\alpha+\beta)$, and is connected flexibly to a distally adjacent one of the plurality of vertebral elements.

2. System according to claim 1, wherein the vertebral elements have through-holes or channels so as to accept flexible cables.

3. System according to claim 1, wherein one of the vertebral elements forms, together with the proximally adjacent vertebrae, a rotational joint with a stroke $\theta$ which is symmetric and in the range of between $-\alpha$ and $+\alpha$.

4. System according to claim 1, wherein a pair of vertebral elements forms an elementary module in which following flexibly connected vertebral elements can rotate with respect to two mutually orthogonal axes P and Y, both orthogonal to the axis of the preceding vertebral element and passing through the edge of the preceding vertebrae and the edge of the same preceding vertebra.

5. System according to claim 2, wherein each one of the holes machined in the vertebral elements has a cylinder-shaped part and a cone-shaped one, a conicity and a depth of the cone-shaped part depending upon the angles of minimum and maximum stroke of $-\alpha$ and $+\alpha$.

6. System according to claim 1, wherein each vertebral element is crossed, in addition to the holes, by at least one more hole devoted to the housing of fiber optics and/or hydraulic or pneumatic tubes, and/or actuation cables for tools mounted on the distal part of the system.

7. System according to claim 1, further comprising a stapling tool disposed on the distal part.

8. System according to claim 7, further comprising a brake to maintain the desired steering of the distal end, according to an operator intention.

9. System according to claim 7, including a handle to actuate the distal tool.

10. System according to claim 8, wherein the stapler is steerable, the stapler steering being actuated by means of a single transmission cable having a mechanism to execute both tissue closure and staples ejection.

11. System according to claim 10 wherein the cartridge is changeable in order to execute multiple sutures by means of the same reusable multifiring monopatient instrument in the same intervention.

12. System according to claim 7, further comprising a double safety mechanism ensuring that the firing of staples is possible only if the tissue has been correctly closed and the operator has intentionally enabled firing.

13. System according to claim 9, wherein the motorized handle is equipped with a local or remote actuator.

14. System according to claim 8, wherein the handle is motorized, and has a local or remote actuator, both the handle and the actuator being reusable in multipatient interventions after sterilization replacement of a disposable sterile cover, the motorized handle being attached to the brake by means of a fast mounting device.

15. System according to claim 9, in which the medial part comprises a flexible or rigid shaft.

16. System according to claim 9, where the distal end can be removed resulting in a rigid motorized stapling tool and the rigid shaft is made to rotate with respect to its longitudinal axis.

* * * * *